US012558104B2

(12) United States Patent
Girouard et al.

(10) Patent No.: US 12,558,104 B2
(45) Date of Patent: Feb. 24, 2026

(54) SURGICAL CUTTING GUIDE

(71) Applicant: Aesculap AG, Tuttlingen (DE)

(72) Inventors: Christophe Girouard, Sarcicourt (FR);
Saïd Moussa, Chamarandes-Choignes
(FR)

(73) Assignee: Aesculap AG, Tuttlingen (DE)

( * ) Notice: Subject to any disclaimer, the term of this
patent is extended or adjusted under 35
U.S.C. 154(b) by 306 days.

(21) Appl. No.: 18/555,788

(22) PCT Filed: Apr. 29, 2022

(86) PCT No.: PCT/EP2022/061444
§ 371 (c)(1),
(2) Date: Oct. 17, 2023

(87) PCT Pub. No.: WO2022/229369
PCT Pub. Date: Nov. 3, 2022

(65) Prior Publication Data
US 2024/0197337 A1 Jun. 20, 2024

(30) Foreign Application Priority Data

Apr. 29, 2021 (EP) ..................................... 21171090

(51) Int. Cl.
*A61B 17/15* (2006.01)
*A61B 17/00* (2006.01)
(52) U.S. Cl.
CPC .. *A61B 17/155* (2013.01); *A61B 2017/00526*
(2013.01)
(58) Field of Classification Search
CPC .............................. A61B 17/15; A61B 17/155
See application file for complete search history.

(56) References Cited

U.S. PATENT DOCUMENTS

| | | | |
|---|---|---|---|
| 2006/0288837 A1 | 12/2006 | Utz et al. | |
| 2013/0325017 A1 | 12/2013 | Lomicka | |
| 2023/0225744 A1* | 7/2023 | Fraone | A61B 17/155 |
| | | | 606/87 |

FOREIGN PATENT DOCUMENTS

| | | |
|---|---|---|
| EP | 2774554 A1 | 9/2014 |
| EP | 3649968 A1 | 5/2020 |
| WO | 2015112566 A1 | 7/2015 |

OTHER PUBLICATIONS

Search Report received in International Application No. PCT/
EP2022/061444 dated Sep. 1, 2022, 4 pages.
Written Opinion received in International Application No. PCT/
EP2022/061444 dated Sep. 1, 2022, 6 pages.
Office Action received in Japanese Application No. 2023-566727
dated Oct. 21, 2025, with translation, 3 pages.

* cited by examiner

*Primary Examiner* — Samuel S Hanna
(74) *Attorney, Agent, or Firm* — Christopher A. Rothe;
CM Law

(57) ABSTRACT

A surgical cutting guide includes a body having at least one
first cutting slot formed between a first cutting guide surface
and an opposing second cutting guide surface. The first
cutting slot extends longitudinally between a first end stop
surface and an opposing second end stop surface. The first
end stop surface has a first convex surface contour and/or the
second end stop surface has a second convex surface con-
tour. The surgical cutting guide can be used in a surgical
procedure, such as a total knee arthroplasty.

17 Claims, 5 Drawing Sheets

SURGICAL CUTTING GUIDE

CROSS-REFERENCE TO RELATED APPLICATIONS

This application is the United States national phase entry of International Application No. PCT/EP2022/061444, filed on Apr. 29, 2022, and claims priority to European Application No. 21171090.0, filed on Apr. 29, 2021. The contents of International Application No. PCT/EP2022/061444 and European Application No. 21171090.0 are incorporated by reference herein in their entireties.

FIELD

The invention relates to a surgical cutting guide, comprising a body having at least one first cutting slot, wherein the first cutting slot is formed between a first cutting guide surface and an opposing second cutting guide surface, and wherein the first cutting slot extends longitudinally between a first end stop surface and an opposing second end stop surface.

BACKGROUND

Such surgical cutting guides are used during orthopedic surgical procedures to assist the surgeon in executing proper bone cuts. For example, a surgeon performing a total knee arthroplasty can make one or several cuts on the distal end of the femur, such as to properly fit a prosthetic femoral component. The surgical cutting guide allows executing more accurate cuts by guiding the used surgical cutting instrument.

US 2013/0325017 A1 discloses a surgical cutting guide including a body with a cutting slot configured to receive a surgical cutting instrument. The cutting slot is formed between two opposing cutting guide surfaces and extends longitudinally between a first end stop surface and an opposing second end stop surface. The opposing end stop surfaces each have a flat surface contour.

SUMMARY

It is an object of the present invention to provide a surgical cutting guide which allows improved guiding of the surgical cutting instrument.

According to the invention, the first end stop surface has a first convex surface contour and/or the second end stop surface has a second convex surface contour. The present inventors have recognized that providing at least one of the two end stop surfaces with a convex surface contour helps to avoid friction and friction-induced wear between the surgical cutting instrument and the first cutting slot. Moreover, providing at least one of the end stop surfaces with a convex surface contour enables a larger longitudinal inclination angle of the surgical cutting instrument within the first cutting slot in comparison to a cutting slot having the same length, but flat end stop surfaces. These benefits result in an improved guiding of the cutting instrument. In a preferred embodiment, the first convex surface contour and/or the second convex surface contour are curved in vertical direction of the first cutting slot. In other words, in a preferred embodiment, the first end stop surface and/or the second end stop surface project into the first cutting slot, thereby causing a variable longitudinal extension of the first cutting slot along its vertical direction. The surgical cutting guide is for use during a surgical procedure. The at least one first cutting slot is configured to receive a surgical cutting instrument. The first cutting guide surface and the second cutting guide surface each can be sized, shaped, or otherwise configured to accommodate the surgical cutting instrument placed against it. Preferably, the first cutting guide surface and the second cutting guide surface each have a flat surface contour. The first cutting guide surface and the second cutting guide surface oppose each other in transverse direction of the first cutting slot. Preferably, the first cutting guide surface and the second cutting guide surface are parallel to each other. The first end stop surface and the second end stop surface oppose each other in longitudinal direction of the first cutting slot. The first end stop surface and the second end stop surface each form a closure of the first cutting slot preventing the cutting instrument from escaping the first cutting slot in the longitudinal direction. Preferably, the first end stop surface and the second end stop surface extend in vertical direction and in transverse direction of the first cutting slot. In a preferred embodiment, the body is formed integrally, i.e. as a single piece of material. In other embodiments, the body can comprise a plurality of separate body parts, which are fixedly or releasably joined together. The body can be manufactured of a metal material and/or a plastic material.

In one embodiment the first convex surface contour and/or the second convex surface contour are curved in vertical direction of the first cutting slot. Preferably, the first convex surface contour and/or the second convex surface contour are flat and/or not curved in transverse direction of the first cutting slot.

In one embodiment the first end stop surface and/or the second end stop surface project into the first cutting slot, thereby causing a variable longitudinal extension of the first cutting slot along its vertical direction. In other words, the length of the first cutting slot varies over its height because of the inwardly curving first convex surface contour and second convex surface contour. Preferably, the width of the first cutting slot does not vary over its length, preferably at least in the area of the first end stop surface and the second end stop surface.

In one embodiment the first end stop surface and/or the second end stop surface extend vertically over an entire vertical height of the first cutting slot in the area of the end stop surfaces. The cutting slot is therefore entirely closed at its opposing ends—i.e., in the area of the end stop surfaces—over its vertical height.

In one embodiment, the first convex surface contour and/or the second convex surface contour is formed by at least one radius, the radius being between 10 mm and 30 mm, preferably between 15 mm and 25 mm, particularly preferably being 18 mm. The present inventors have recognized that a radius between 10 mm and 30 mm has the benefit of providing reduced friction and friction-induced wear for many different common types and/or sizes of surgical cutting instruments. In this context it was found that a radius between 15 mm and 25 mm is particularly advantageous for surgical cutting instruments used during total knee arthroplasty. In one embodiment, the first convex surface contour and the second convex surface contour have the same radius. In other embodiments, the first convex surface contour is formed by a first radius and the second convex surface contour is formed by a different second radius.

In one embodiment, the first convex surface contour and/or the second convex surface contour is defined by a plurality of tangential radii. This allows an improved adaption of the first convex surface contour and/or the second convex surface contour to a specific cutting procedure and/or a specific surgical cutting instrument to be used. Preferably, the radii are within the intervals mentioned in the context of the previous embodiment.

In one embodiment, the first cutting guide surface is formed on an inner side of a first wall portion, included in or coupled to the body, and the second cutting guide surface is formed on an opposing inner side of a second wall portion, included in or coupled to the body. The inner side of the first wall portion and the inner side of the second wall portion face each other in transverse direction of the first cutting slot. In one embodiment, the first wall portion and the second wall portion form an integral body segment of the body. In other embodiments, the first wall portion and the second wall portion are formed as separate parts being fixedly or releasably joined together.

In one embodiment, the first end stop surface is formed on an inner side of a third wall portion, included in or coupled to the body, and the second end stop surface is formed on an inner side of a fourth wall portion, included in or coupled to the body, wherein the third wall portion and the fourth wall portion each extend in transverse direction of the first cutting slot between the first wall portion and the second wall portion. The inner side of the third wall portion and the inner side of the fourth wall portion face each other in longitudinal direction of the first cutting slot. In one embodiment, the first wall portion, the second wall portion, the third wall portion and the fourth wall portion form an integral body segment of the body. In other embodiments at least one of said wall portions is formed as a separate body part and fixedly or releasably joined together with at least one other of said wall portions.

In one embodiment, the first wall portion has at least one first surface reduction recess extending between the inner side and an opposing outer side of the first wall portion and/or the second wall portion has at least one second surface reduction recess extending between the inner side and an opposing outer side of the second wall portion. The first surface reduction recess causes a reduction of the first cutting guide surface. The second reduction recess causes a reduction of the second cutting guide surface. The reduction of the first cutting guide surface and/or second cutting guide surface leads to a further reduction of friction and friction-induced wear between the surgical cutting instrument and the first cutting slot. The first surface reduction recess extends into the first wall portion in transverse direction of the first cutting slot. In one embodiment, the first surface reduction recess is formed as a pocket countersunk into the inner side of the first wall portion. In another embodiment, the first surface reduction recess is formed as an aperture within the first wall portion. The same holds analogously with respect to the second surface reduction recess.

In one embodiment, the first surface reduction recess forms a first aperture and/or the second surface reduction recess forms a second aperture. The first aperture extends from the inner side to the outer side of the first wall portion in transverse direction of the first cutting slot. The second aperture extends from the inner side to the outer side of the second wall portion in transverse direction of the first cutting slot. This embodiment allows for a simplified cleaning and sterilization. In addition, the first aperture and/or the second aperture allow for an improved visibility of the surgical cutting instrument within the first cutting slot. Moreover, a reduction of material used and thus less weight can be achieved.

In one embodiment, the first wall portion has a plurality of surface reduction recesses defining a first recess pattern and the second wall portion has a plurality of second surface reduction recesses defining a different second recess pattern. The different recess patterns ensure that the surgical cutting instrument is in contact with and guided by at least one of the first cutting guide surface or the second cutting guide surface. In contrast to this, equal recess patterns can lead to opposite areas of the surgical cutting instrument having no contact at the same time. This can be disadvantageous under certain circumstances. In one embodiment, at least one of the first and second recess patterns is formed as aperture pattern having a plurality of surface reduction apertures.

In one embodiment, the first wall portion, the second wall portion, the third wall portion and the fourth wall portion form an integral first cutting slot body segment of the body. The first cutting slot body segment forms a single piece of material. In one embodiment, the first cutting slot body segment is produced by an additive manufacturing process. The present inventors have recognized that this allows for a particularly simple and cost-effective design. This is all the more true if the first wall portion and the second wall portion have surface reduction recesses and/or apertures. In one embodiment, the first cutting slot body segment is integral with remaining segments of the body. In other embodiments, the first cutting slot body segment is formed as a separate body part and fixedly or releasably joined together with other segments and/or parts of the body.

In one embodiment, the first cutting slot body segment— in a viewing direction normal to the outer side of the first wall portion—has an outer contour comprising a flat inferior contour portion and a convex superior contour portion. The flat inferior contour portion ensures that the first cutting slot body segment can be placed flat and securely positioned on the bone to be cut. The present inventors have recognized that the convex superior contour portion allows for an improved handling of the surgical cutting guide by the operating surgeon. In addition, material and thus weight can be saved. This allows for an even easier handling. The convex superior contour portion causes a variable height of the first cutting slot body segment along the longitudinal direction of the first cutting slot. In the area of the third and the fourth wall portion—and therefore at the ends of the first cutting slot—the height of the first cutting slot body segment is comparatively low. The height is comparatively high in a longitudinally central area of the first cutting slot.

In one embodiment, the body comprises a bone engagement body segment having an inferior bone engagement surface, the bone engagement body segment and the first cutting slot body segment being spaced apart from each other to form at least one bone viewing aperture. The at least one bone viewing aperture allows for an improved visibility of the target bone below the surgical cutting guide. This improved visibility helps the operating surgeon to align and position the surgical cutting guide on the bone to be cut. Moreover, the at least one bone viewing aperture allows for a further reduction of material and thus less weight. This leads to further reduced manufacturing costs and improved manual handling. The inferior bone engagement surface is configured to engage with the bone to be cut. In one embodiment, the bone engagement body segment comprises at least one through-hole configured for receiving a fixation element for fixing the bone engagement body segment to the bone to be cut. In one embodiment, the bone engagement body segment and the first cutting slot body segment form an integral portion of the body. In other embodiments, the bone engagement body segment and the first cutting slot body segment are formed as separate parts of the body. In this case the bone engagement body segment and the first cutting slot body segment can be fixedly or releasably joined together. The bone engagement body segment and the first cutting slot body segment are spaced apart from each other in transverse direction of the first cutting slot. In one embodiment the bone engagement body segment has a block-like shape and the first cutting slot body segment has a ledge-like form. Preferably, the bone engagement body segment comprises further cutting slots, in particular a third cutting slot and a fourth cutting slot, with convex end stop surface contours. Preferably, said further cutting slots a chamfer slots configured to guide chamfer cuts on the distal femur.

In one embodiment, the first cutting slot body segment and the bone engagement body segment are connected by means of a strut body segment having at least a first strut and a second strut spaced apart from each other in longitudinal direction of the first cutting slot to form the at least one bone viewing aperture. The first strut and the second strut each are elongated in transverse direction of the first cutting slot. A first end of the first strut is connected to the bone engagement body segment and a second end of the first strut is connected to the first cutting slot body segment. The same holds analogously for the second strut. This embodiment helps to further reduce the weight of the body and allows for a comparatively large bone viewing aperture. In one embodiment, the first cutting slot body segment, the bone engagement body segment and the strut body segment form an integral body portion of the body. In other embodiments, at least one of said body segments is formed as separate body part and fixedly or releasably joined together with at least one other of said body segments.

In one embodiment, the first cutting slot body segment and/or the bone engagement body segment and/or the strut body segment are formed integrally by an additive manufacturing process. In a preferred embodiment, the entire body and/or surgical cutting guide is formed integrally by said additive manufacturing process. In one embodiment, the additive manufacturing process uses a 3D printing technology for metal and/or plastic materials.

In one embodiment, the body, in particular a second cutting slot body segment of the body, comprises a second cutting slot having end stop surfaces with convex surface contours. Concerning further features of the second cutting slot and its end stop surfaces, reference is made to the disclosure concerning the first cutting slot. The disclosure concerning the first cutting slot applies mutatis mutandis to the second cutting slot. Preferably, the second cutting slot extends in parallel to the first cutting slot. Preferably, the second cutting slot body segment opposes the first cutting slot body segment in transverse direction. Preferably, the second cutting slot body segment is arranged on an opposing side of the bone engagement body segment. Preferably, the first cutting slot is configured to guide an anterior resection of the distal femur and the second cutting slot is configured to guide a posterior resection of the distal femur or vice versa.

In one embodiment, the body, in particular the bone engagement body segment of the body, comprises a third cutting slot and a fourth cutting slot each having end stop surfaces with convex surface contours. Concerning further features of the third cutting slot and its end stop surfaces and the fourth cutting slot and its end stop surfaces, reference is made to the disclosure concerning the first cutting slot. The disclosure concerning the first cutting slot applies mutatis mutandis to the third cutting slot and the fourth cutting slot. Preferably, the third and fourth cutting slots extends in parallel to each other. Preferably, the third and fourth cutting slots extend in parallel to the first cutting slot. Preferably, the bone engagement body segment connects the first cutting slot body segment to the second cutting slot body segment. Preferably, the third and fourth cutting slots are configured to guide chamfer resections, i.e. chamfer cuts, on the distal femur.

BRIEF DESCRIPTION OF THE DRAWINGS

In the following, a preferred embodiment of the invention will be described in detail with reference to the drawings. Throughout the drawings, the same elements will be denoted by the same reference numerals.

DETAILED DESCRIPTION

Figure 1:
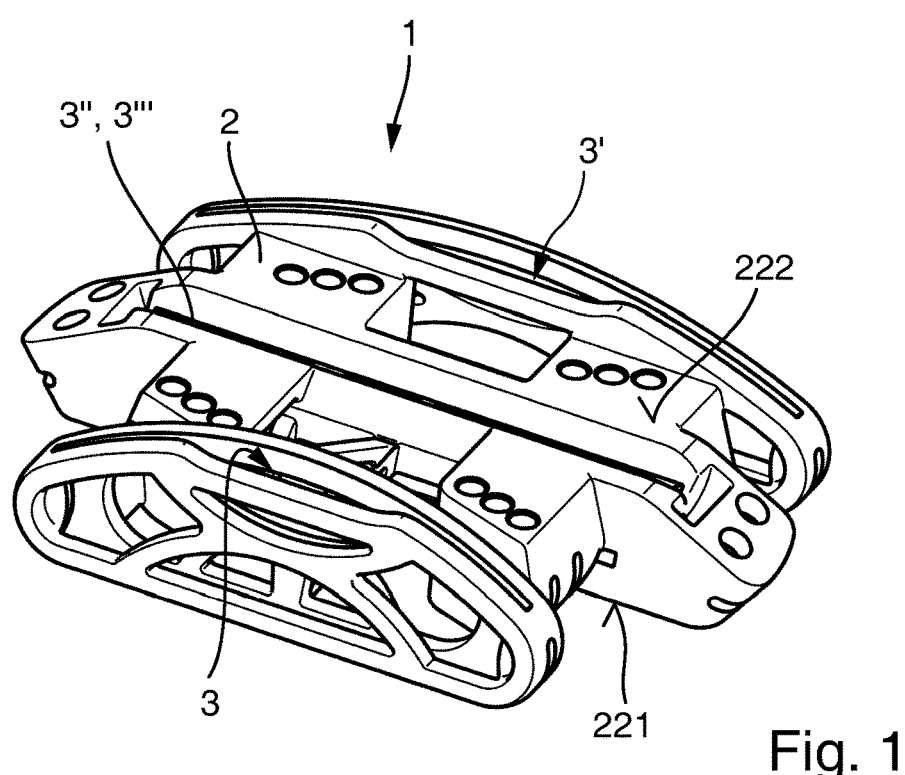
FIG. 1 is a perspective view an embodiment of a surgical cutting guide.
Figure 2:
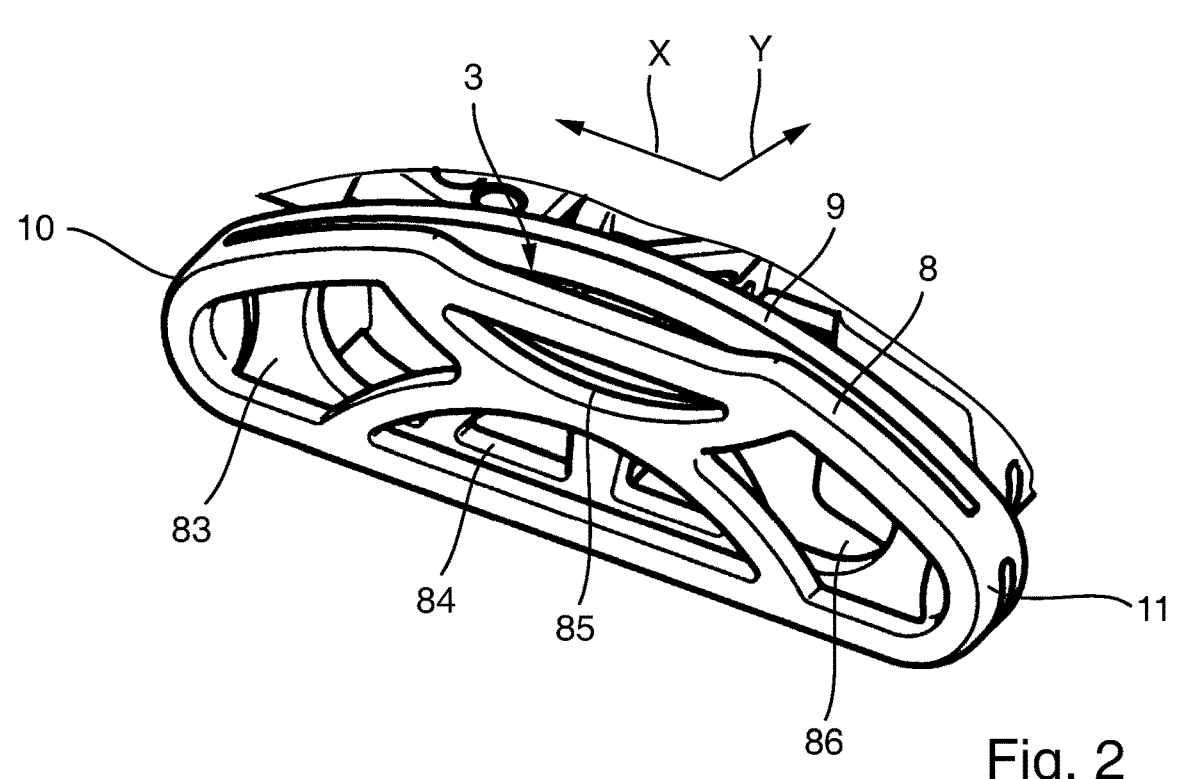
FIG. 2 is a perspective detail view of the surgical cutting guide according to FIG. 1 in an area of a first cutting slot.

According to FIG. 1, a surgical cutting guide 1 is provided for use in a surgical procedure. The surgical cutting guide 1 can be used to prepare the distal end of a femur B (FIG. 4) for a total knee arthroplasty procedure. A surgeon performing such a total knee arthroplasty can make several cuts on the distal end of the femur B, in order to properly fit a prosthetic femoral component. The surgical cutting guide 1 is configured to guide an according surgical cutting instrument, such as a saw or the like. Guiding the surgical cutting instrument by means of the surgical cutting guide 1 allows for an improved accuracy of the delivered cuts.

Figure 3:
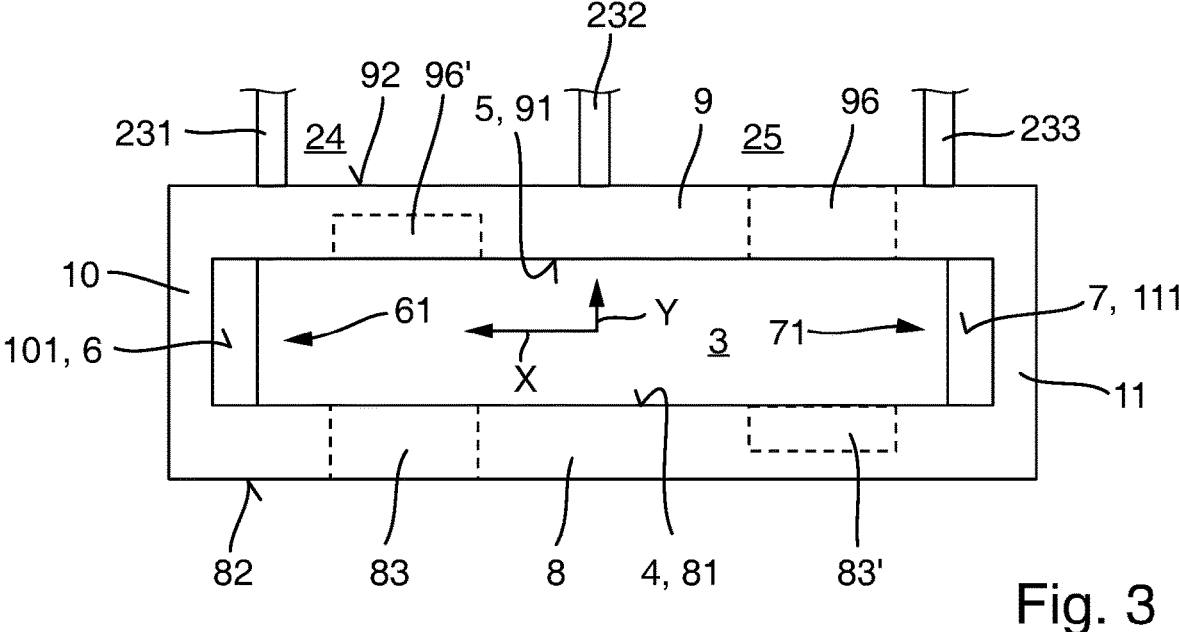
FIG. 3 is a simplified top view of the surgical cutting guide according to FIGS. 1 and 2 in the area of the first cutting slot.

The surgical cutting guide 1 comprises a body 2 having at least one first cutting slot 3. The first cutting slot 3 is formed between a first cutting guide surface 4 and an opposing second cutting guide surface 5 (FIG. 3). The first cutting guide surface 4 and the second cutting guide surface 5 oppose each other in transverse direction Y of the first cutting slot 3. The first cutting slot 3 extends longitudinally between a first end stop surface 6 and an opposing second end stop surface 7. The first end stop surface 6 and the second end stop surface 7 oppose each other in longitudinal direction X of the first cutting slot 3.

The first cutting slot 3 is configured to receive the surgical cutting instrument in its vertical direction. Once inserted into the first cutting slot 3, the surgical cutting instrument fits snugly between the first cutting guide surface 4 and the second cutting guide surface 5 in transverse direction Y. The first cutting guide surface 4 and the second cutting guide surface 5 guide the surgical cutting instrument along the longitudinal direction X and vertically, wherein the first end stop surface 6 and the second end stop surface 7 prevent the surgical cutting instrument from escaping the first cutting slot 3. In order to cut the target bone, in this case the distal femur B, the surgical cutting instrument moves relatively to the first and second cutting guide surfaces 4, 5 and the first and second end stop surfaces 6, 7. This relative movement causes friction as well as friction-induced wear.

The present inventors have recognized that providing at least one of the end stop surfaces 6, 7 with a convex surface contour results in reduced friction and friction-induced wear. In the embodiment as shown, both end stop surfaces 6, 7 have a convex surface contour. As such, the first end stop surface 6 has a first convex surface contour 61 and the second end stop surface 7 has a second convex surface contour 71. Due to their convex shape, the first end stop surface 6 and the second end stop surface 7 are each curved along the vertical direction of the first cutting slot 3. In other words the first end stop surface 6 and the second end stop surface 7 each curve inwards the first cutting slot 3 with respect to the longitudinal direction X.

Figure 6:
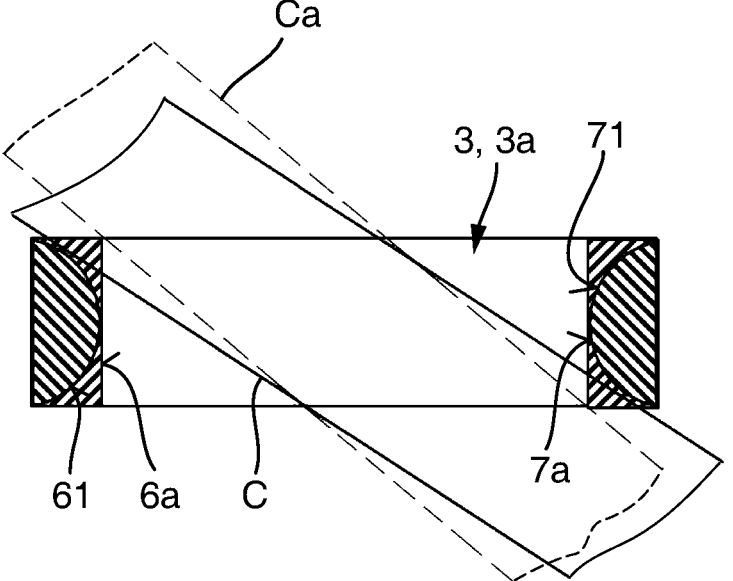
FIG. 6 is a simplified sectional view in order to illustrate a benefit of the design of the surgical cutting guide.
Figure 7:
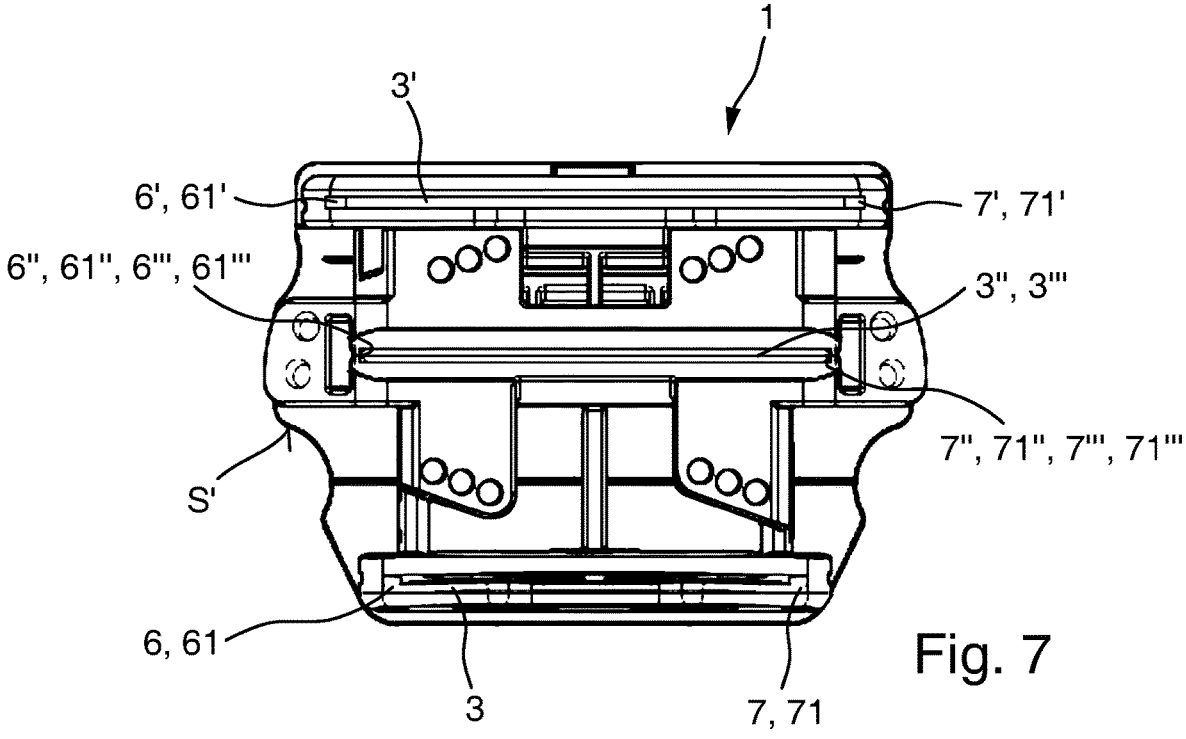
FIG. 7 is a further top view of the surgical cutting guide together with an outer contour of a surgical cutting guide known from prior art.

FIG. 6 illustrates further benefits of the first and second convex surface contours 61, 71. In FIG. 6 two exemplary configurations are schematically superimposed:

In a first configuration an exemplary surgical cutting instrument C is inserted into the first cutting slot 3 and inclined along the longitudinal direction X. Because of said inclination, opposing edges of the surgical cutting instrument C contact the first convex surface contour 61 and the second convex surface contour 72, respectively.

Within the superimposed second configuration the surgical cutting instrument is inserted in a cutting slot 3a having opposing flat end stop surfaces 6a, 7a. In the second configuration the surgical cutting instrument is referenced as Ca. A comparison of the first configuration and the second configuration illustrates that providing the end stop surfaces with convex surface contours allows for a greater inclination angle in comparison to a cutting slot having the same length and flat end stop surfaces. Moreover, the convex surface contours allow for a reduction of the cutting slot length by approximately 10% in comparison to flat end stop surfaces. The present inventors have further recognized that the convex surface contours 61, 71 help to stabilize the surgical cutting instrument C during cutting in its inclined orientation. Moreover, the convex surface contours 61, 71 help to decrease the contact load on the opposing edges of the surgical cutting instrument C. Decreasing the contact load leads to the already mentioned reduction of friction and friction-induced wear. In contrast to this, inclining the surgical cutting instrument Ca between the flat end stop surfaces 6a, 7a leads to a sharp point contact, which can result in increased friction and wear.

In the embodiment shown, the first convex surface contour 61 is formed by a radius R, the radius being 18 mm. In other embodiments, the radius can range between 10 mm and 30 mm. The same may apply with respect to the second convex surface contour 71. However, in the embodiment shown, the second convex surface contour 71 is defined by a plurality of tangential radii R1, R2, R3. Said radii R1, R2, R3 range between 10 mm and 30 mm. In other embodiments, the first convex surface contour 61 and the second convex surface contour 71 are formed by one and the same radius.

In the embodiment shown, the first cutting guide surface 4 is formed on an inner side 81 of a first wall portion 8, which is shown in more detail in FIG. 3. The second cutting guide surface 5 is formed on an opposing inner side 91 of a second wall portion 9. The first wall portion 8 and the second wall portion 9 oppose each other in transverse direction Y of the first cutting slot 3. The inner side 81 of the first wall portion 8 and the inner side 91 of the second wall portion 9 are, in the embodiment shown, parallel to each other. Thus, the same holds with respect to the first cutting guide surface 4 and the second cutting guide surface 5. The first wall portion 8 and the second wall portion 9 each can be included or coupled to the body 2, which will be described in more detail below.

With reference to FIG. 3, the first end stop surface 6 is formed on an inner side 101 of a third wall portion 10. The second end stop surface 7 is formed on an inner side 111 of a fourth wall portion 11. The third wall portion 10 and the fourth wall portion 11 oppose each other in longitudinal direction X of the first cutting slot 3. The third wall portion 10 and the fourth wall portion 11 each extend in transverse direction Y of the first cutting slot 3 between the first wall portion 8 and the second wall portion 9. Both, the third wall portion 10 and the fourth wall portion 11, can be included in or coupled to the body 2, which will be described in more detail below.

Figure 5:
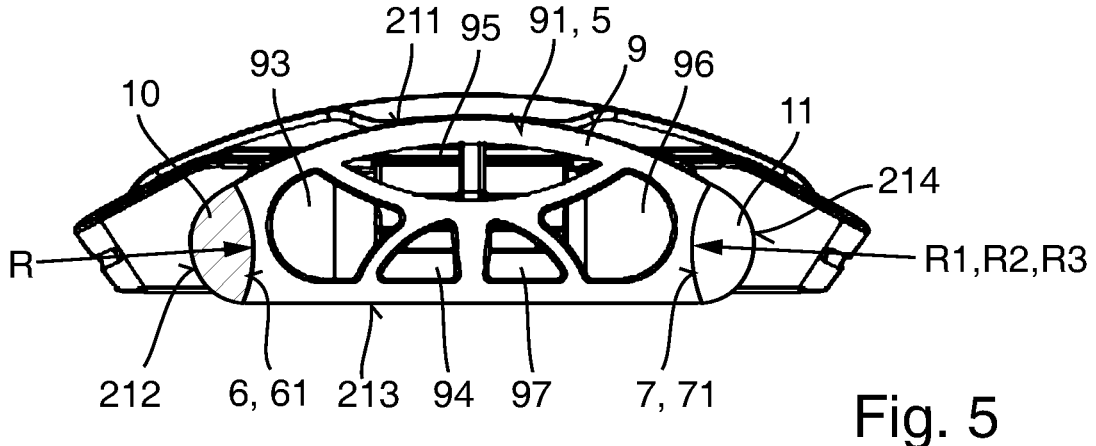
FIG. 5 shows the surgical cutting guide in a sectional view along a sectional line V-V according to FIG. 4.

In the embodiment shown, the first wall portion 8 has a plurality of surface reduction apertures 83, 84, 85, 86 defining a first aperture pattern within the first wall portion 8. Said surface apertures recesses 83, 84, 85, 86 can also be denoted as windows, breakthroughs or the like. As is shown in FIG. 5 in more detail, the second wall portion 9 comprises a plurality of surface reduction apertures 93, 94, 95, 96, 97 defining a second aperture pattern. The apertures 93, 94, 95, 96, 97 form windows and/or breakthroughs within the second wall portion 9. In other embodiments, only one of the first and the second wall portions 8, 9 comprises one or more apertures.

The apertures 83, 84, 85, 86 within the first wall portion 8 serve to reduce the amount of contact between the surgical cutting instrument and the first cutting guide surface 4. In other words, said apertures 83, 84, 85, 86 reduce the first cutting guide surface 4 in comparison to an embodiment that does not comprise apertures within the first wall portion. The same holds analogously with respect to the apertures 93, 94, 95, 96, 97 within the second wall portion 9 and their effect on the second cutting guide surface 5. Moreover, providing said apertures 83 to 86 and 93 to 97 within the first wall portion 8 and the second wall portion 9, respectively, improves visibility of the surgical cutting instrument C within the first cutting slot 3. As an additional benefit, providing said apertures 83 to 86 and 93 to 97 helps to reduce the overall weight of the surgical cutting guide 1, which improves manual handling during the surgical procedure.

FIG. 3 further illustrates that still other embodiments comprise recesses instead of apertures. For illustrative purposes FIG. 3 shows a first recess 83' within the first wall portion 8, the first recess 83' extending between the inner side 81 and the opposing outer side 82 of the first wall portion 8. The first recess 83' is countersunk into the inner side 81 in transverse direction Y of the first cutting slot 3. Analogously, the second wall portion 9 can comprise a second recess 96' extending between the inner side 91 and an opposing outer side 92 of the second wall portion. The second recess 96' is countersunk into the inner side 91 in transverse direction Y of the first cutting slot.

Figure 4:
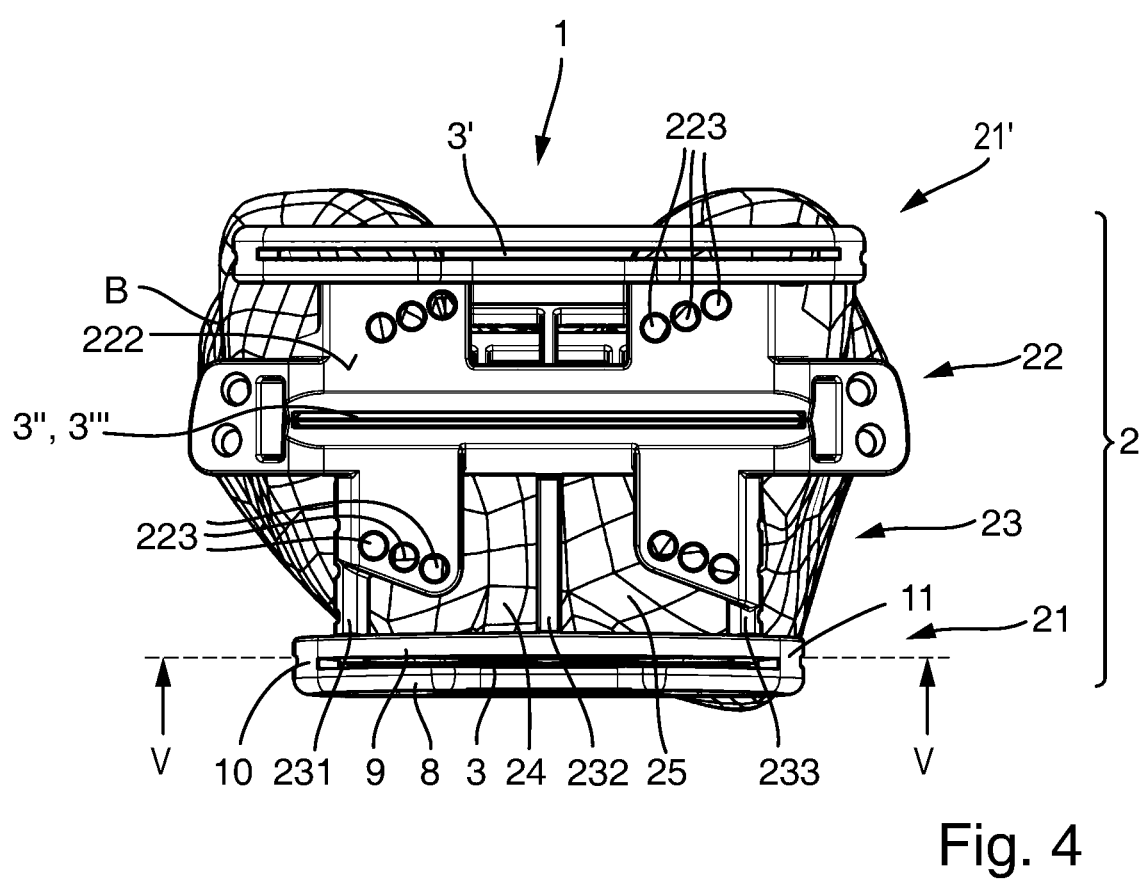
FIG. 4 is a further top view of the surgical cutting guide, wherein the surgical cutting guide is placed on a distal end of a femur to be cut.

In the embodiment shown, the first wall portion 8, the second wall portion 9, the third wall portion 10 and the fourth wall portion 11 form an integral first cutting slot body segment 21 of the body 2 (FIG. 4). The first cutting slot body segment 21 forms a single and/or unitary piece of material.

Further with reference to FIG. 4, the body 2 comprises, in the embodiment shown, a bone engagement body segment 22, which is configured for engagement with the bone to be cut, in this case the distal femur B. The bone engagement body segment 22 comprises an inferior bone engagement surface 221 (see FIG. 1), which opposes a superior surface 222. The inferior bone engagement surface 221 and the superior surface 222 oppose each other in vertical direction of the first cutting slot 3. The inferior bone engagement surface 221 can comprise a post, bolt or other fixation element for releasable fixation of the surgical cutting guide 1 to the target bone. In the embodiment shown, the bone engagement body segment 22 comprises a plurality of through-holes 223 which extend between the superior surface 222 and the inferior bone engagement surface 221. Said through-holes 223 are configured to receive a fixation element or the like. The bone engagement body segment 22, in the embodiment shown, is formed as a single and/or unitary piece of material.

The first cutting slot body segment 21 and the bone engagement body segment 22 are spaced apart from each other to form at least one bone viewing aperture 24, 25. In the embodiment shown, two bone viewing apertures 24, 25 are formed, which can be denoted as first bone viewing aperture 24 and second bone viewing aperture 25. In order to form said bone viewing apertures 24, 25, the bone engagement body segment 22 and the first cutting slot body segment 21 are spaced apart along the transverse direction Y of the first cutting slot 3. As is shown in FIG. 4, the bone viewing apertures 24, 25 allow for an improved visibility of the target bone and thus for an improved positioning and alignment of the surgical cutting guide 1. Moreover, providing the bone viewing apertures 24, 25 further helps to reduce the overall weight of the surgical cutting guide 1.

In the embodiment shown, the first cutting slot body segment 21 and the bone engagement body segment 22 are connected by means of a strut body segment 23 of the body 2. The strut body segment 23, in the embodiment shown, comprises a first strut 231, a second strut 232 and a third strut 233 which are spaced apart from each other in longitudinal direction X of the first cutting slot 3. In other embodiments, the strut body segment 23 comprises only a single, two or more than three struts.

The first strut 231, the second strut 232 and the third strut 233 each have an elongated and/or slender shape. The first strut element 231, the second strut element 232 and the third strut element 233 each extend in transverse direction Y of the first cutting slot 3, wherein a first end of each of the struts is connected to the bone engagement body segment 22 and a second end of each strut is connected to the first cutting slot body segment 21.

The first bone viewing aperture 24 extends between the first strut 231 and the second strut 232 in longitudinal direction X and between the first cutting slot body segment 21 and the bone engagement body segment 22 in transverse direction Y of the first cutting slot 3. The second bone viewing aperture 25 extends between the second strut 232 and the third strut 233 in longitudinal direction X and between the first cutting slot body segment 21 and the bone engagement body segment 22 in transverse direction Y of the first cutting slot 3.

In the embodiment shown, the first cutting slot body segment 21 has an outer contour 211, 212, 213, 214 (see FIG. 5), which comprises a convex superior contour portion 211, a flat inferior contour portion 213 and opposing outer end contour portions 212, 214. The convex superior contour portion 211 and the flat inferior contour portion 213 oppose each other in vertical direction of the first cutting slot 3. The outer end contour portions 212, 214 oppose each other in longitudinal direction X of the first cutting slot 3. In the embodiment shown, the outer end contour portions 212, 214 each have a convex shape. The flat inferior contour portion 213 allows for an improved alignment and positioning of the surgical cutting guide 1 on the target bone. The convex superior contour portion 211 helps to reduce the bulkiness of the body. Moreover, the convex shape of the superior contour portion 211 as well as the convex shape of the outer end contour portions 212, 214 causes less impairment and/or injury of body tissue during the surgical procedure in comparison to a flat contour shape.

In the embodiment shown, the body 2 comprises a second cutting slot body segment 21'. In other embodiments, only a single cutting slot body segment or more than two cutting slot body segments are provided.

The second cutting slot body segment 21' opposes the first cutting slot body segment 21 in transverse direction Y and is arranged on an opposing side of the bone engagement body segment 22. The second cutting slot body segment 21' is, in the embodiment shown, slightly longer than the first cutting slot body segment 21. Apart from this, the second cutting slot body segment 21' is identical. Hence, what has been disclosed with regard to the first cutting slot body segment 21 also applies mutatis mutandis with regard to the second cutting slot body segment 21'. Therefore, further explanations in regard of the second cutting slot body segment 21' are not necessary.

In the embodiment shown, the first cutting slot body segment 21, the bone engagement body segment 22, the strut body segment 23 and the second cutting slot body segment 21' are formed integrally by an additive manufacturing process. Thus, the body 2 forms an integral, single and/or unitary piece of material. In the embodiment shown, a 3D printing process is used for additive manufacturing of the unitary body 2. The body 2—and thus its body segments 21, 22, 23, 21'—are made, more particularly 3D printed, from a metal material. In other embodiments, a synthetic material, like plastic material is used.

In the embodiment shown, the second cutting slot body segment 21' comprises a second cutting slot 3' having end stop surfaces 6', 7' with convex surface contours 61', 71'. The second cutting slot 3' extends parallel to the first cutting slot 3. Concerning shape, form, function and/or additional features of the second cutting slot 3', in particular its end stop surfaces 6', 7', reference is made to the description of the first cutting slot 3. Said description applies mutatis mutandis. In the embodiment shown, the first cutting slot 3 is configured to guide an anterior cut on the distal femur and the second cutting slot 3' is configured to guide a posterior cut on the distal femur or vice versa.

In the embodiment shown, the bone engagement body segment 22 comprises a third cutting slot 3" having end stop surfaces 6", 7" with convex surface contours 61", 71" and a fourth cutting slot 3''' having end stop surfaces 6''', 7''' with convex surface contours 61''', 71'''. The third and fourth cutting slots 3", 3''' extend parallel to the first and second cutting slots 3, 3'. The third and fourth cutting slots 3", 3"" are inclined in vertical direction and in opposite. Concerning the further shape, form, function and/or additional features of the third and fourth cutting slots 3", 3", in particular their end stop surfaces 6", 7", 6''', 7''', reference is made the description of the first cutting slot 3. Said description applies mutatis mutandis. In the embodiment shown, the third and fourth cutting slot 3", 3''' are configured to guide chamfer cuts on the distal femur.

Figure 8:
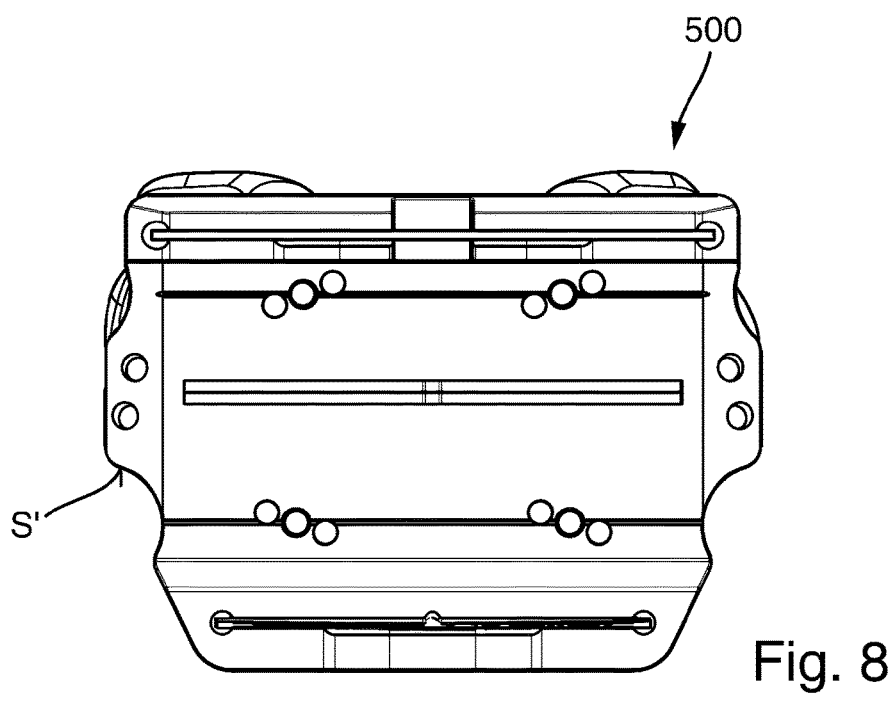
FIG. 8 is a top view of a prior art surgical cutting guide.

FIG. 8 shows a surgical cutting guide 500 known from prior art. Apparently, the surgical cutting guide 500 has a rather bulky shape S', which can cause a rather high weight and thus, high material cost and suboptimal handling during the surgical procedure.

In contrast to this, the surgical cutting guide 1 has a reduced bulkiness, which allows for a reduced weight, reduced material costs, improved handling and improved bone visibility during the surgical procedure.

The invention claimed is:

1. A surgical cutting guide comprising:

a body having a top side, a bottom side, and a first cutting slot extending from the top side to the bottom side such that the first cutting slot is open through the top side and open through the bottom side, the first cutting slot formed between a first cutting guide surface and a second cutting guide surface opposite the first cutting guide surface, the first cutting guide surface and the second cutting guide surface separated from one another by a slot width, the first cutting slot extending longitudinally between a first end stop surface and a second end stop surface opposite the first end stop surface, the first end stop surface and the second end stop surface separated from one another by a cutting slot length that is greater than the cutting slot width, the first end stop surface comprising a first convex surface contour facing into the slot and/or the second end stop surface comprising a second convex surface contour facing into the slot, and the first convex surface contour and/or the second convex surface contour defining an arc having an arc length that extends from the top side of the body to the bottom side of the body.

2. The surgical cutting guide according to claim 1, wherein the first convex surface contour and/or the second convex surface contour are curved in a vertical direction of the first cutting slot.

3. The surgical cutting guide according to claim 1, wherein the first end stop surface and/or the second end stop surface project into the first cutting slot, thereby causing a variable longitudinal extension of the first cutting slot along the vertical direction.

4. The surgical cutting guide according to claim 1, wherein the first end stop surface and/or the second end stop surface extend vertically over an entire vertical height of the first cutting slot.

5. The surgical cutting guide according to claim 1, wherein the first convex surface contour and/or the second convex surface contour is formed by at least one radius that is between 10 mm and 30 mm.

6. The surgical cutting guide according to claim 1, wherein the first convex surface contour and/or the second convex surface contour is defined by a plurality of tangential radii.

7. The surgical cutting guide according to claim 1, wherein the first cutting guide surface is formed on an inner side of a first wall portion, included in or coupled to the body, and the second cutting guide surface is formed on an opposing inner side of a second wall portion, included in or coupled to the body.

8. The surgical cutting guide according to claim 7, wherein the first end stop surface is formed on an inner side of a third wall portion, included in or coupled to the body, the second end stop surface is formed on an inner side of a fourth wall portion, included in or coupled to the body, wherein the third wall portion and the fourth wall portion each extend in transverse direction of the first cutting slot between the first wall portion and the second wall portion.

9. The surgical cutting guide according to claim 8, wherein the first wall portion, the second wall portion, the third wall portion and the fourth wall portion form an integral first cutting slot body segment of the body.

10. The surgical cutting guide according to claim 9, wherein the body comprises a bone engagement body segment having an inferior bone engagement surface, the bone engagement body segment and the first cutting slot body segment being spaced apart from each other to form at least one bone viewing aperture.

11. The surgical cutting guide according to claim 10, wherein the first cutting slot body segment and the bone engagement body segment are connected by a strut body segment having at least a first strut and a second strut spaced apart from the first strut in a longitudinal direction of the first cutting slot to form the at least one bone viewing aperture.

12. The surgical cutting guide according to claim 11, wherein the first cutting slot body segment and/or the bone engagement body segment and/or the strut body segment are formed integrally by an additive manufacturing process.

13. The surgical cutting guide according to claim 11, wherein the body comprises a second cutting slot having end stop surfaces with convex surface contours.

14. The surgical cutting guide according to claim 13, wherein the body comprises a third cutting slot and a fourth cutting slot each having end stop surfaces with convex surface contours.

15. The surgical cutting guide according to claim 7, wherein the first wall portion has at least one first surface reduction recess extending between the inner side and an opposing outer side of the first wall portion and/or the second wall portion has at least one second surface reduction recess extending between the inner side and an opposing outer side of the second wall portion.

16. The surgical cutting guide according to claim 15, wherein the first surface reduction recess forms a first aperture and/or the second surface reduction recess forms a second aperture.

17. The surgical cutting guide according to claim 15, wherein the at least one first surface reduction recess comprises a plurality of surface reduction recesses defining a first recess pattern, and the at least one second surface reduction recess comprises a plurality of second surface reduction recesses defining a second recess pattern that is different from the first recess pattern.

* * * * *